(12) United States Patent
Voloshin-Sela et al.

(10) Patent No.: US 12,357,821 B2
(45) Date of Patent: Jul. 15, 2025

(54) USING INTERLEAVED COOLING PERIODS TO INCREASE THE PEAK INTENSITY OF TUMOR TREATING FIELDS

(71) Applicant: Novocure GmbH, Root (CH)

(72) Inventors: Tali Voloshin-Sela, Haifa (IL); Lilach Avigdor, Haifa (IL); Reuven Shamir, Zichron Ya'akov (IL)

(73) Assignee: Novocure GmbH, Baar (CH)

( * ) Notice: Subject to any disclaimer, the term of this patent is extended or adjusted under 35 U.S.C. 154(b) by 230 days.

(21) Appl. No.: 18/128,721

(22) Filed: Mar. 30, 2023

(65) Prior Publication Data

US 2023/0310848 A1 Oct. 5, 2023

Related U.S. Application Data

(60) Provisional application No. 63/325,230, filed on Mar. 30, 2022.

(51) Int. Cl.
*A61N 1/36* (2006.01)
*A61N 1/08* (2006.01)

(52) U.S. Cl.
CPC ........... *A61N 1/36002* (2017.08); *A61N 1/08* (2013.01)

(58) Field of Classification Search
None
See application file for complete search history.

(56) References Cited

U.S. PATENT DOCUMENTS

| 6,868,289 | B2 | 3/2005 | Palti |
| 7,016,725 | B2 | 3/2006 | Palti |
| 7,089,054 | B2 | 8/2006 | Palti |
| 7,136,699 | B2 | 11/2006 | Palti |
| 7,333,852 | B2 | 2/2008 | Palti |
| 7,467,011 | B2 | 12/2008 | Palti |
| 7,519,420 | B2 | 4/2009 | Palti |
| 7,565,205 | B2 | 7/2009 | Palti |

(Continued)

FOREIGN PATENT DOCUMENTS

| KR | 20160134469 A | 11/2016 |
| WO | 2020225599 A1 | 11/2020 |

OTHER PUBLICATIONS

International Search Report and Written Opinion issued in application No. PCT/IB2023/053151 dated Jun. 23, 2023.

*Primary Examiner* — Michael W Kahelin
(74) *Attorney, Agent, or Firm* — Potomac Law Group, PLLC (57) ABSTRACT

Alternating electric fields (e.g., TTFields) may be induced in a target region in a subject's body by applying, during each of a plurality of first time intervals, a series of pulses of alternating current between electrode elements positioned on or in the subject's body. Immediately following each first interval of time, the electrode elements are allowed to cool. Although the pulses of alternating current within any given first time interval have amplitudes at a level that would cause overheating if the series of pulses was allowed to continue for one hour, each series of pulses does not, in fact, continue for one hour. To the contrary, each series of pulses is short enough to avoid overheating. Interleaving the cooling periods between the pulsing periods enables higher-current pulses to be used, and the use of those higher-current pulses can advantageously improve the efficacy of treatment.

7 Claims, 8 Drawing Sheets

(56) References Cited

U.S. PATENT DOCUMENTS

| | | |
|---|---|---|
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Paiti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,440,068 B2 | 9/2016 | Palti et al. |
| 9,655,669 B2 | 5/2017 | Palti et al. |
| 9,750,934 B2 | 9/2017 | Palti et al. |
| 9,910,453 B2 | 3/2018 | Wasserman et al. |
| 10,188,851 B2 | 1/2019 | Wenger et al. |
| 10,441,776 B2 | 10/2019 | Kirson et al. |
| 10,779,875 B2 | 9/2020 | Palti et al. |
| 10,967,167 B2 | 4/2021 | Hagemann et al. |
| 11,103,698 B2 | 8/2021 | Chang et al. |
| 11,191,956 B2 | 12/2021 | Giladi et al. |
| 2004/0176804 A1 | 9/2004 | Palti |
| 2005/0209642 A1 | 9/2005 | Palti |
| 2006/0167499 A1 | 7/2006 | Palti |
| 2006/0276858 A1 | 12/2006 | Palti |
| 2007/0225766 A1 | 9/2007 | Palti |
| 2007/0239213 A1 | 10/2007 | Palti |
| 2009/0076366 A1 | 3/2009 | Palti |
| 2012/0029419 A1 | 2/2012 | Palti |
| 2012/0283726 A1 | 11/2012 | Palti |
| 2014/0330268 A1 | 11/2014 | Palti et al. |
| 2017/0120041 A1 | 5/2017 | Wenger et al. |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2018/0280687 A1 | 10/2018 | Carter et al. |
| 2019/0117956 A1 | 4/2019 | Wenger et al. |
| 2019/0117963 A1 | 4/2019 | Travers et al. |
| 2019/0224474 A1 | 7/2019 | Yang et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0114141 A1 | 4/2020 | Bomzon et al. |
| 2020/0114142 A1 | 4/2020 | Bomzon et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1* | 5/2020 | Wasserman ............... A61N 1/08 |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0269037 A1 | 8/2020 | Hagemann et al. |
| 2020/0269041 A1 | 8/2020 | Zeevi et al. |
| 2020/0269042 A1 | 8/2020 | Gliadi et al. |
| 2020/0368525 A1 | 11/2020 | Maag et al. |
| 2021/0031031 A1 | 2/2021 | Wasserman et al. |
| 2021/0038584 A1 | 2/2021 | Voloshin-Sela |
| 2021/0060334 A1 | 3/2021 | Avraham et al. |
| 2021/0069503 A1 | 3/2021 | Tran et al. |
| 2021/0138233 A1 | 5/2021 | Deslauriers |
| 2021/0162228 A1 | 6/2021 | Urman et al. |
| 2021/0177492 A1 | 6/2021 | Travers et al. |
| 2021/0187277 A1 | 6/2021 | Wasserman et al. |
| 2021/0196348 A1 | 7/2021 | Wasserman |
| 2021/0199640 A1 | 7/2021 | Patel et al. |
| 2021/0203250 A1 | 7/2021 | Wasserman |
| 2021/0268247 A1 | 9/2021 | Story et al. |
| 2021/0299440 A1 | 9/2021 | Deslauriers et al. |
| 2021/0308446 A1 | 10/2021 | Alon et al. |
| 2021/0330950 A1 | 10/2021 | Hagemann et al. |
| 2021/0346694 A1 | 11/2021 | Wasserman et al. |
| 2021/0379362 A1 | 12/2021 | Smith et al. |
| 2021/0408383 A1 | 12/2021 | Kalra et al. |
| 2022/0095997 A1 | 3/2022 | Wasserman |
| 2022/0096821 A1 | 3/2022 | Kirson et al. |
| 2022/0118249 A1 | 4/2022 | Bomzon et al. |
| 2022/0161028 A1 | 5/2022 | Giladi et al. |
| 2022/0193435 A1 | 6/2022 | Wasserman et al. |
| 2022/0267445 A1 | 8/2022 | Tran et al. |
| 2022/0280787 A1 | 9/2022 | Bomzon et al. |
| 2022/0288395 A1 | 9/2022 | Voloshin-Sela et al. |
| 2022/0313992 A1 | 10/2022 | Wasserman |
| 2022/0323753 A1 | 10/2022 | Voloshin-Sela et al. |
| 2022/0387784 A1 | 12/2022 | Kirson et al. |
| 2022/0395699 A1 | 12/2022 | Doyle |
| 2022/0409893 A1 | 12/2022 | Wasserman et al. |
| 2023/0000384 A1 | 1/2023 | Wasserman et al. |
| 2023/0001197 A1 | 1/2023 | Wasserman et al. |
| 2023/0001221 A1 | 1/2023 | Farber |
| 2023/0009366 A1 | 1/2023 | Voloshin-Sela et al. |
| 2023/0019638 A1 | 1/2023 | Wasserman |
| 2023/0037806 A1 | 2/2023 | Wasserman et al. |
| 2023/0043071 A1 | 2/2023 | Wasserman et al. |
| 2023/0098801 A1 | 3/2023 | Carlson |
| 2023/0141087 A1 | 5/2023 | Giladi et al. |
| 2023/0188055 A1 | 6/2023 | Wasserman |

\* cited by examiner

PRIOR ART

FIG. 10 though a subsequent series of pulses of alternating current can be applied without causing the at least one first electrode element to exceed the temperature threshold and without causing the at least one second electrode element to exceed the temperature threshold.

USING INTERLEAVED COOLING PERIODS TO INCREASE THE PEAK INTENSITY OF TUMOR TREATING FIELDS

CROSS REFERENCE TO RELATED APPLICATIONS

This application claims the benefit of U.S. Provisional Application 63/325,230, filed Mar. 30, 2022, which is incorporated herein by reference in its entirety.

BACKGROUND

Tumor Treating Fields, or TTFields, are alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. 200 kHz TTFields are FDA approved for the treatment of glioblastoma (GBM). Alternating electric fields at frequencies between 50 kHz and 1 MHz can also be used to treat medical conditions other than tumors. For example, as described in U.S. Pat. No. 10,967,167 (which is incorporated herein by reference in its entirety), alternating electric fields e.g., at 50-200 kHz can increase the permeability of the blood brain barrier (BBB) so that, e.g., chemotherapy drugs can reach the brain. And as described in U.S. Pat. No. 11,103,698 (which is incorporated herein by reference in its entirety), alternating electric fields e.g., at 50-500 kHz can increase the permeability of cell membranes so that large molecules can traverse cell membranes.

Optune® is the standard approach for delivering TTFields to living subjects. Optune® includes a field generator and two pairs of transducer arrays (i.e., electrode arrays) that are placed on the patient's shaved head. One pair of arrays (L/R) is positioned to the left and right of the tumor, and the other pair of arrays (A/P) is positioned anterior and posterior to the tumor. In the preclinical setting, TTFields can also be applied in vitro using, for example, the prior art Inovitro™ TTFields lab bench system. In both Optune® and Inovitro™, the field generator (a) applies an AC voltage between the L/R transducer arrays (or electrodes) for 1 second, which induces an electric field through the tumor in one direction; then (b) applies an AC voltage between the A/P transducer arrays (or electrodes) for 1 second, which induces an electric field through the tumor in another direction; then repeats that two-step sequence (a) and (b) for the duration of the treatment.

SUMMARY OF THE INVENTION

One aspect of this application is directed to a first method of inducing an alternating electric field in a target region in a subject's body. The first method comprises applying, during each of a plurality of first time intervals, a series of pulses of alternating current between at least one first electrode element and at least one second electrode element, wherein the at least one first electrode element and the at least one second electrode element are positioned on or in the subject's body; and allowing the at least one first electrode element and the at least one second electrode element to cool during each of a plurality of second time intervals. Each of the plurality of second time intervals immediately follows a respective one of the plurality of first time intervals. The pulses of alternating current within any given first time interval have amplitudes at a level that would cause at least one of the first electrode elements to exceed a temperature threshold between 37° C. and 43° C. if the series of pulses was allowed to continue for one hour. But the series of pulses within each first time interval is actually short enough to prevent the at least one first electrode element from exceeding the temperature threshold and to prevent the at least one second electrode element from exceeding the temperature threshold.

In some instances of the first method, each of the plurality of second time intervals is at least as long as an immediately preceding first time interval. In some instances of the first method, each of the plurality of second time intervals is at least 5 minutes. In some instances of the first method, each of the second time intervals is long enough so that a subsequent series of pulses of alternating current can be applied without causing the at least one first electrode element to exceed the temperature threshold and without causing the at least one second electrode element to exceed the temperature threshold.

In some instances of the first method, the temperature threshold is between 38° C. and 40° C. In some instances of the first method, all the pulses of alternating current within any given one of the first time intervals have the same amplitude. In some instances of the first method, during each of the first time intervals, the amplitudes of the pulses of alternating current ramp up from an initial level to a final level and subsequently remain at the final level for the duration of the first time interval.

In some instances of the first method, the step of allowing the at least one first electrode element and the at least one second electrode element to cool during each of a plurality of second time intervals is implemented by not applying pulses of alternating current between the at least one first electrode element and the at least one second electrode element during the second time intervals.

In some instances of the first method, the step of allowing the at least one first electrode element and the at least one second electrode element to cool during each of a plurality of second time intervals is implemented by applying, during each of the plurality of second time intervals, a series of second amplitude pulses of alternating current between the at least one first electrode element and the at least one second electrode element, wherein each series of second amplitude pulses has an average amplitude that is less than one half the average amplitude of the series of pulses in the immediately preceding first time interval.

In some instances of the first method, the plurality of first time intervals includes at least 100 first time intervals, and the plurality of second time intervals includes at least 100 second time intervals. Optionally, in these embodiments, each of the plurality of first time intervals is at least one minute long, each of the plurality of second time intervals is at least one minute long, and each series of pulses includes at least 50 pulses.

Another aspect of this application is directed to a second method of inducing an alternating electric field in a target region in a subject's body. The second method comprises applying, during each of a plurality of first time intervals, a series of pulses of alternating current between at least one first electrode element and at least one second electrode element. The at least one first electrode element and the at least one second electrode element are positioned on or in the subject's body. The second method also comprises allowing the at least one first electrode element and the at least one second electrode element to cool during each of a plurality of second time intervals, wherein each of the plurality of second time intervals immediately follows a respective one of the plurality of first time intervals. The second method also comprises applying, during each of a plurality of third time intervals, a series of pulses of alternating current between at least one third electrode element and at least one fourth electrode element, wherein the at least one third electrode element and the at least one fourth electrode element are positioned on or in the subject's body. And the second method also comprises allowing the at least one third electrode element and the at least one fourth electrode element to cool during each of a plurality of fourth time intervals, wherein each of the plurality of fourth time intervals immediately follows a respective one of the plurality of third time intervals. The pulses of alternating current within any given first time interval have amplitudes at a first level that would cause at least one of the first electrode elements to exceed a temperature threshold between 37° C. and 43° C. if the series of pulses was allowed to continue for one hour. But the series of pulses within each first time interval is actually short enough to prevent the at least one first electrode element from exceeding the temperature threshold and to prevent the at least one second electrode element from exceeding the temperature threshold. Similarly, the pulses of alternating current within any given third time interval have amplitudes at a second level that would cause at least one of the third electrode elements to exceed the temperature threshold if the series of pulses was allowed to continue for one hour. But the series of pulses within each third time interval is actually short enough to prevent the at least one third electrode element from exceeding the temperature threshold and to prevent the at least one fourth electrode element from exceeding the temperature threshold.

In some instances of the second method, each of the plurality of second time intervals is at least as long as an immediately preceding first time interval, and each of the plurality of fourth time intervals is at least as long as an immediately preceding third time interval.

In some instances of the second method, the pulses of alternating current within the first time intervals and the pulses of alternating current within the third time intervals have amplitudes that are independently controllable. In some instances of the second method, the amplitudes of the pulses of alternating current within the first time intervals differ from the amplitudes of the pulses of alternating current within the third time intervals.

In some instances of the second method, each of the plurality of second time intervals is at least 5 minutes, and each of the plurality of fourth time intervals is at least 5 minutes. In some instances of the second method, each of the plurality of first time intervals is at least 10 minutes, and each of the plurality of third time intervals is at least 10 minutes.

In some instances of the second method, each of the second time intervals is long enough so that a subsequent series of pulses of alternating current can be applied without causing at the at least one first electrode element to exceed the temperature threshold and without causing the at least one second electrode element to exceed the temperature threshold, and each of the fourth time intervals is long enough so that a subsequent series of pulses of alternating current can be applied without causing the at least one third electrode element to exceed the temperature threshold and without causing the at least one fourth electrode element to exceed the temperature threshold.

In some instances of the second method, the temperature threshold is between 38° C. and 40° C. In some instances of the second method, all the pulses of alternating current within any given one of the first time intervals have the same amplitude. In some instances of the second method, during each of the first time intervals, the amplitudes of the pulses of alternating current ramp up from an initial level to a final level and subsequently remain at the final level for the duration of the first time interval.

In some instances of the second method, each third interval of time overlaps with a respective first interval of time. In some instances of the second method, each third interval of time is mutually exclusive with all the first intervals of time, and each first interval of time is mutually exclusive with all the third intervals of time.

In some instances of the second method, the step of allowing the at least one first electrode element and the at least one second electrode element to cool during each of a plurality of second time intervals is implemented by not applying pulses of alternating current between the at least one first electrode element and the at least one second electrode element during the second time intervals. And the step of allowing the at least one third electrode element and the at least one fourth electrode element to cool during each of a plurality of fourth time intervals is implemented by not applying pulses of alternating current between the at least one third electrode element and the at least one fourth electrode element during the fourth time intervals.

In some instances of the second method, the step of allowing the at least one first electrode element and the at least one second electrode element to cool during each of a plurality of second time intervals is implemented by applying, during each of the plurality of second time intervals, a series of second amplitude pulses of alternating current between the at least one first electrode element and the at least one second electrode element, wherein each series of second amplitude pulses has an average amplitude that is less than one half the average amplitude of the series of pulses in the immediately preceding first time interval. And the step of allowing the at least one third electrode element and the at least one fourth electrode element to cool during each of a plurality of fourth time intervals is implemented by applying, during each of the plurality of fourth time intervals, a series of fourth amplitude pulses of alternating current between the at least one third electrode element and the at least one fourth electrode element, wherein each series of fourth amplitude pulses has an average amplitude that is less than one half the average amplitude of the series of pulses in the immediately preceding third time interval.

In some instances of the second method, the plurality of first time intervals includes at least 100 first time intervals, the plurality of second time intervals includes at least 100 second time intervals, the plurality of third time intervals includes at least 100 third time intervals, and the plurality of fourth time intervals includes at least 100 second fourth intervals. Optionally, in these embodiments, each of the plurality of first time intervals is at least one minute long, each of the plurality of second time intervals is at least one minute long, each of the plurality of third time intervals is at least one minute long, each of the plurality of fourth time intervals is at least one minute long, and each series of pulses includes at least 50 pulses.

Another aspect of the invention is directed to a first apparatus for inducing an alternating electric field in a target region in a subject's body. The first apparatus comprises a pulse generator and a controller. The pulse generator is configured to generate a series of pulses of alternating current between a first output terminal and a second output terminal, with an amplitude that depends on a state of at least one control input. The controller is configured to send signals to the at least one control input that cause the pulse generator to output pulses having a first amplitude between the first output terminal and the second output terminal during each of a plurality of first time intervals. The controller is further configured to, during each of a plurality of second time intervals, each of which immediately follows a respective one of the plurality of first time intervals, either (i) send signals to the at least one control input that cause the pulse generator not to output pulses during each of the plurality of second time intervals or (ii) send signals to the at least one control input that cause the pulse generator to output pulses having a second amplitude between the first output terminal and the second output terminal during each of a plurality of second time intervals, wherein the second amplitude is less than half the first amplitude. The controller is further configured to accept at least one first input signal from at least one first temperature sensor and to accept at least one second input signal from at least one second temperature sensor. The plurality of first time intervals includes at least 10 first time intervals, the plurality of second time intervals includes at least 10 second time intervals, each of the plurality of first time intervals is at least one minute long, each of the plurality of second time intervals is at least one minute long, and each series of pulses includes at least 10 pulses.

In some embodiments of the first apparatus, the controller is further configured to adjust the first amplitude during each of the plurality of first time intervals based on the at least one first input signal and the at least one second input signal. In some embodiments of the first apparatus, each of the plurality of second time intervals is at least 5 minutes long. In some embodiments of the first apparatus, the controller is further configured to end a given first time interval based on the at least one first input signal and the at least one second input signal. In some embodiments of the first apparatus, the controller is further configured to end a given second time interval based on the at least one first input signal and the at least one second input signal.

Another aspect of the invention is directed to a second apparatus for inducing an alternating electric field in a target region in a subject's body. The second apparatus comprises a pulse generator and a controller. The pulse generator is configured to generate a series of pulses of alternating current between a first output terminal and a second output terminal, with an amplitude that depends on a state of at least one control input. The controller is configured to send signals to the at least one control input that cause the pulse generator to output pulses having a first amplitude between the first output terminal and the second output terminal during each of a plurality of first time intervals. The controller is further configured to, during each of a plurality of second time intervals, each of which immediately follows a respective one of the plurality of first time intervals, either (i) send signals to the at least one control input that cause the pulse generator not to output pulses during each of the plurality of second time intervals or (ii) send signals to the at least one control input that cause the pulse generator to output pulses having a second amplitude between the first output terminal and the second output terminal during each of a plurality of second time intervals, wherein the second amplitude is less than half the first amplitude. The controller is further configured to accept at least one first input signal from at least one first temperature sensor and to accept at least one second input signal from at least one second temperature sensor. The plurality of first time intervals includes at least 10 first time intervals, the plurality of second time intervals includes at least 10 second time intervals, each of the plurality of first time intervals is at least one minute long, each of the plurality of second time intervals is at least one minute long, and each series of pulses includes at least 10 pulses.

In the second apparatus, the pulse generator is further configured to generate a series of pulses of alternating current between a third output terminal and a fourth output terminal, with an amplitude that depends on a state of the at least one control input. The controller is further configured to send signals to the at least one control input that cause the pulse generator to output pulses having a third amplitude between the third output terminal and the fourth output terminal during each of a plurality of third time intervals. The controller is further configured to, during each of a plurality of fourth time intervals, each of which immediately follows a respective one of the plurality of third time intervals, either (i) send signals to the at least one control input that cause the pulse generator not to output pulses during each of the plurality of fourth time intervals or (ii) send signals to the at least one control input that cause the pulse generator to output pulses having a fourth amplitude between the third output terminal and the fourth output terminal during each of a plurality of fourth time intervals, wherein the fourth amplitude is less than half the third amplitude. The controller is further configured to accept at least one third input signal from at least one third temperature sensor and to accept at least one fourth input signal from at least one fourth temperature sensor. The plurality of third time intervals includes at least 10 third time intervals. The plurality of fourth time intervals includes at least 10 fourth time intervals. Each of the plurality of third time intervals is at least one minute long, and each of the plurality of fourth time intervals is at least one minute long.

In some embodiments of the second apparatus, the controller is further configured to adjust the first amplitude during each of the plurality of first time intervals based on the at least one first input signal and the at least one second input signal, and to adjust the third amplitude during each of the plurality of third time intervals based on the at least one third input signal and the at least one fourth input signal.

In some embodiments of the second apparatus, the controller is further configured to end a given first time interval based on the at least one first input signal and the at least one second input signal, and configured to end a given third time interval based on the at least one third input signal and the at least one fourth input signal.

In some embodiments of the second apparatus, the controller is further configured to end a given second time interval based on the at least one first input signal and the at least one second input signal, and to end a given fourth time interval based on the at least one third input signal and the at least one fourth input signal.

Some embodiments of the second apparatus further comprise at least one first electrode element wired up to the first output terminal; at least one second electrode element wired up to the second output terminal; at least one third electrode element wired up to the third output terminal; and at least one fourth electrode element wired up to the fourth output terminal.

Optionally, in the embodiments described in the previous paragraph, the first temperature sensor comprises a first thermistor in thermal contact with the at least one first electrode element, the second temperature sensor comprises a second thermistor in thermal contact with the at least one second electrode element, the third temperature sensor comprises a third thermistor in thermal contact with the at least one third electrode element, and the fourth temperature sensor comprises a fourth thermistor in thermal contact with the at least one fourth electrode element.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

When treating subjects using TTFields, higher intensity electric fields are strongly correlated with higher efficacy of treatment; and increasing the electric field's intensity can be achieved by increasing the current that is applied to the electrode arrays. But the current cannot simply be increased to any desired level. This is because increasing the current causes the electrode arrays to heat up. And the temperature of the electrode arrays must never exceed a safety threshold value.

Figure 1:
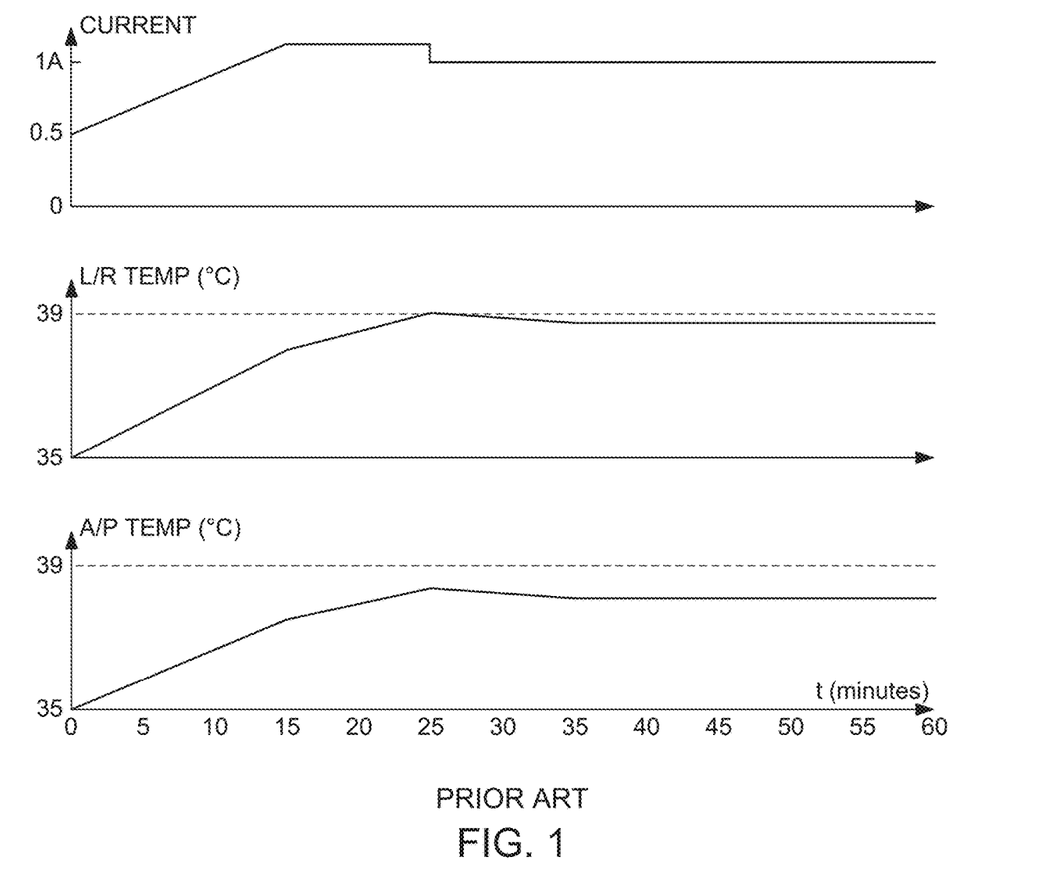
FIG. 1 is a schematic representation of how the prior art Optune® system keeps the temperature of the electrode arrays below a safety threshold.

FIG. 1 is a schematic representation of how the prior art Optune® system keeps the temperature of the electrode arrays below the safety threshold by adjusting the current of the pulses of alternating current that are applied to the electrode arrays. More specifically, when the system is first turned on, it will begin by outputting pulses of alternating current with initial level of current (e.g., 0.5 amp). The system subsequently ramps up the current of the pulses of alternating current from that initial level while continuously monitoring the temperature at all four electrode arrays (using a plurality of thermistors positioned at each of the four electrode arrays), until the hottest array gets close to the predetermined temperature threshold (e.g., 39° C.). In the FIG. 1 example, the left/right electrode arrays are running hotter than the anterior/posterior electrode arrays, so the temperature of the left/right arrays will be the limiting factor.

When the hottest array gets close to the temperature threshold (i.e., at t=15 in the FIG. 1 example, when the current of each pulse is about 1.1 A), the system stops increasing the current of the pulses of alternating current (i.e., it holds the level constant), and continues to monitor the temperature of all four electrode arrays. If at some point the temperature at the hottest array reaches the temperature threshold (e.g., at t=25 in the FIG. 1 example), the system will reduce the current of the pulses of alternating current to keep the temperature of all the electrode arrays below the temperature threshold.

Figure 2A:
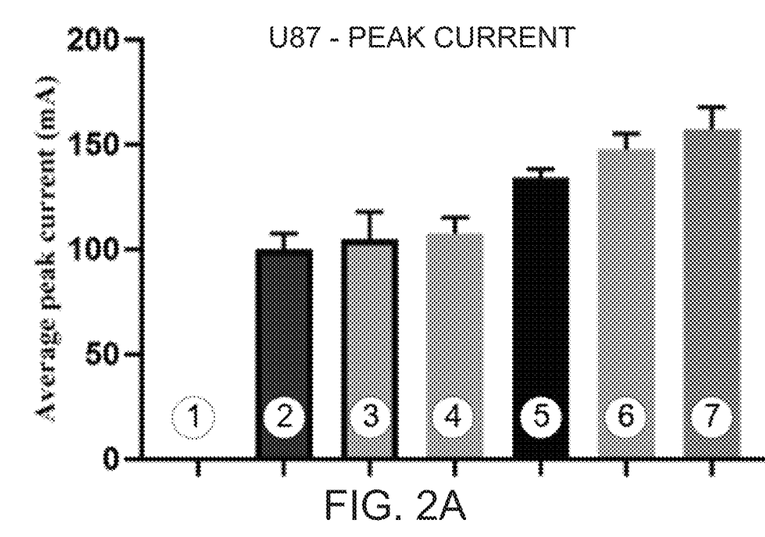
FIG. 2A depicts the result of experiments that measured the peak current for six differently-shaped pulses of alternating current.
Figure 2B:
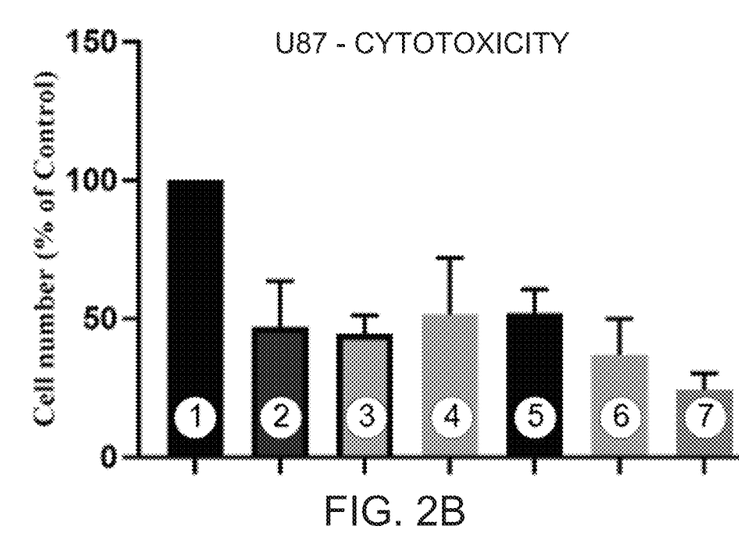
FIG. 2B depicts the result of experiments that measured cytotoxicity for the six differently-shaped pulses of alternating current.

Similar to Optune®, the Inovitro™ TTFields lab bench system automatically adjusts the AC current that is applied to the electrodes to keep the sample dishes at 37° C. FIGS. 2A and 2B depict the results of experiments performed using an Inovitro™ system that was modified to apply pulses of alternating current with different shapes to sample dishes containing U87 cells, to ascertain, for each of the differently-shaped pulses of alternating current, (1) the peak current that was being used when the temperature stabilized at 37° C. and (2) cytotoxicity. TTFields were applied as follows in these experiments: (a) AC current was applied to the L/R electrodes for 1 second or a portion thereof; (b) AC current was applied to the A/P electrodes for 1 second or a portion thereof; and the two-step sequence (a) and (b) was repeated for the duration of the 120 hour experiment.

FIG. 2A depicts the peak current for each of the differently-shaped pulses of alternating current. Bar #1 represents the control, which was not treated with TTFields. Bar #2 represents the peak current when the AC current jumped immediately from zero to the peak at the start of each 1 second interval, and jumped immediately from the peak to zero at the end of each 1 second interval. Bar #3 represents the peak current when the AC current ramped up from zero to the peak in the first 50 ms of each 1 second interval, and ramped down from the peak to zero in the last 50 ms of each 1 second interval. This means that the AC current remained at its peak value for 900 ms in each 1 second interval. Bar #4 represents the peak current when the AC current ramped up from zero to the peak in the first 100 ms of each 1 second interval, and ramped down from the peak to zero in the last 100 ms of each 1 second interval. This means that the AC current remained at its peak value for 800 ms in each 1 second interval.

Bar #5 represents the peak current when the AC current ramped up from zero to the peak in the first 300 ms of each 1 second interval, and ramped down from the peak to zero in the last 300 ms of each 1 second interval. This means that the AC current remained at its peak value for 400 ms in each 1 second interval. Bar #6 represents the peak current when the AC current ramped up from zero to the peak in the first 350 ms of each 1 second interval, and ramped down from the peak to zero in the last 350 ms of each 1 second interval. This means that the AC current remained at its peak value for 300 ms in each 1 second interval. Bar #7 represents the peak current when the AC current ramped up from zero to the peak in the first 400 ms of each 1 second interval, and ramped down from the peak to zero in the last 400 ms of each 1 second interval. This means that the AC current remained at its peak value for 200 ms in each 1 second interval.

FIG. 2B depicts the cytotoxicity results obtained for each of the differently-shaped pulses of alternating current. Each of the numbered bars in FIG. 2B corresponds to a respective numbered bar in FIG. 2A. Notably, the best cytotoxicity results were obtained for bars #6 and 7.

Additional experiments similar to those described above in connection with FIGS. 2A/2B were performed on U87 and 118 cell lines, for a total of six experiments involving a total of 231 dishes. A causality analysis found that the Pearson's correlation coefficient was 0.78 between the peak current and the cytotoxicity, and 0.25 between the rise/fall times of the differently-shaped pulses of alternating current and the cytotoxicity. From this data, it is reasonable to conclude that TTFields with higher peak currents that are applied for a smaller percentage of time are more effective than TTFields with lower peak currents that are applied for a larger percentage of time.

As explained above, the prior art Optune® system generates a series of pulses of alternating current, and selects a current level for those pulses of alternating current that will not cause any of the electrode arrays to overheat (i.e., exceed a predetermined temperature threshold), even when the series of pulses of alternating current continues indefinitely.

In contrast, the embodiments described below take advantage of the conclusion that TTFields with higher peak currents that are applied for a smaller percentage of time are more effective than TTFields with lower peak currents that are applied for a larger percentage of time. More specifically, the embodiments described below set the current of the pulses of alternating current at a level that would cause at least one electrode element to exceed the temperature threshold if the series of pulses was allowed to continue for one hour. The reader may now be wondering: if the current is set at this level, why don't these embodiments overheat? The answer is that the series of pulses is not allowed to continue for one hour. To the contrary, each series of pulses of alternating current ends before any of the electrode elements exceed the temperature threshold, and is followed immediately by a cooling-down period (during which the temperature of the electrode elements drops). The subsequent series of high-current pulses of alternating current does not begin until after the temperature has dropped sufficiently.

Figure 3:
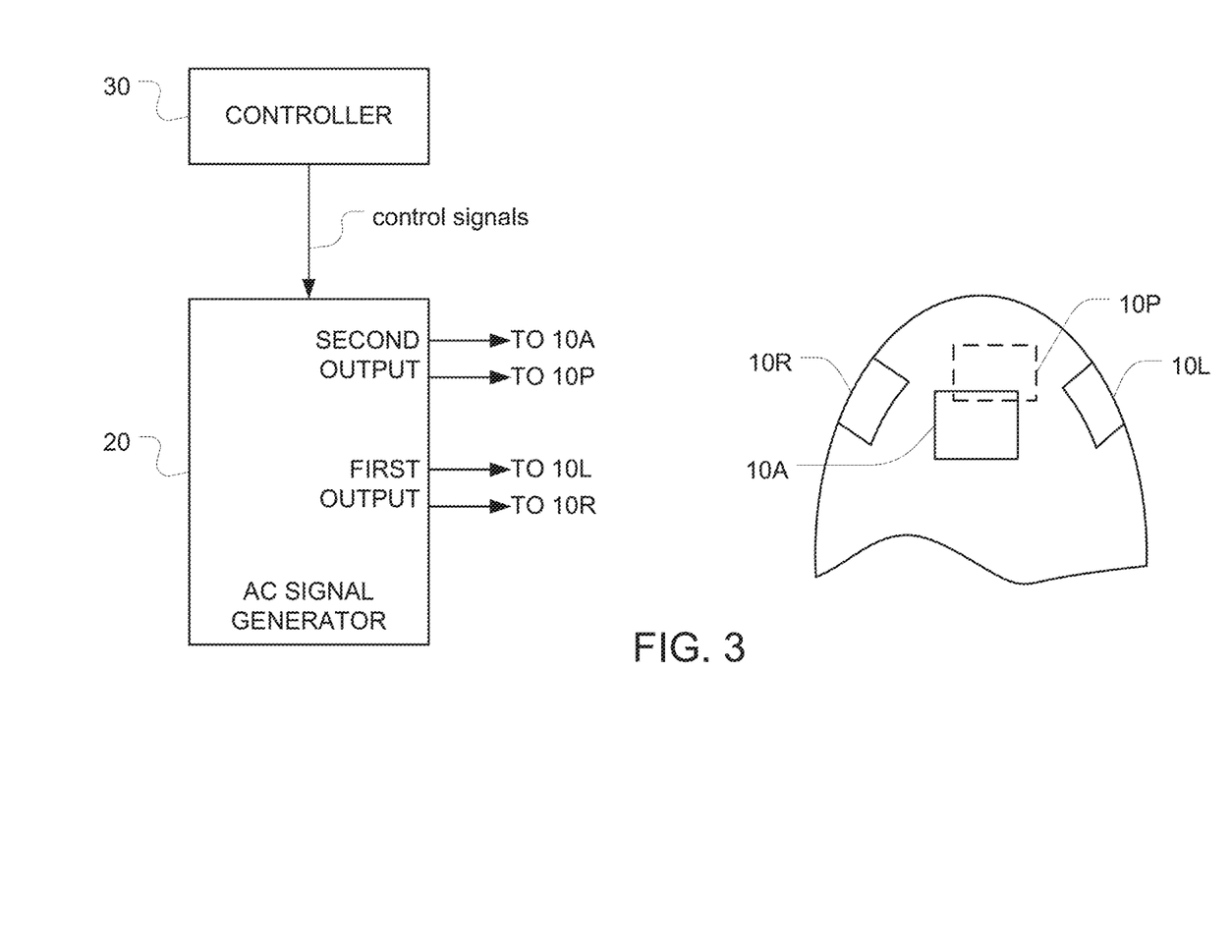
FIG. 3 is a block diagram of an embodiment that can drive a set of transducer arrays with pulses of AC current with the amplitude profiles described herein.

FIG. 3 is a block diagram of an embodiment that can drive a set of transducer arrays 10 with pulses of AC current with the amplitude profiles described herein. The system includes an AC signal generator 20 that is designed to generate first and second AC outputs at a frequency between 50 kHz and 1 MHz. When the system is used to apply TTFields to a portion of a person's body (as shown in FIG. 3), the first AC output is applied across a first pair of electrodes 10L and 10R that are positioned to the left and right of the tumor; and the second AC output is applied across a second pair of electrodes 10A and 10P that are positioned anterior and posterior to a tumor. The AC signal generator 20 could also be used to apply TTFields to an in vitro culture (not shown) by applying the first AC output to electrodes positioned on the left and right walls of an Inovitro™ dish and applying the second AC output to electrodes positioned on the front and back walls of the Inovitro™ dish. In either case, the voltages generated by the AC signal generator 20 should be high enough to drive a current that induces an electric field of at least 1 V/cm in at least a portion of the cancer cells. In some embodiments, the voltages generated by the AC signal generator 20 drive currents that induce electric fields of between 1 V/cm and 10 V/cm in at least a portion of the cancer cells. In some embodiments, the voltages generated by the AC signal generator 20 are at least 75 V RMS.

The AC signal generator 20 is configured to generate first and second AC outputs such that the first and second AC outputs have independently controllable amplitudes that depend on a state of at least one control input. A controller 30 continuously sends control signals to the at least one control input, and these control signals are configured to cause the first and second AC outputs to generate signals with the amplitude profiles described herein. Note that although FIG. 3 depicts the controller 30 and the AC signal generator 20 as two distinct blocks, those two blocks may be integrated into a single hardware device.

The details of the construction of the controller 30 and the nature of the control signals will depend on the design of the AC signal generator 20. In one example, the design of the AC signal generator 20 is similar to the AC signal generator described in U.S. Pat. No. 9,910,453, which is incorporated herein by reference in its entirety. This particular AC signal generator has two output channels (i.e., a first channel for L/R and a second channel for A/P). The instantaneous AC output voltage on either channel depends on the instantaneous output voltage of a DC-DC converter, and the output voltage of that DC-DC converter is controlled by writing control words to a digital-to-analog converter (DAC) e.g., at a 1 ms update rate.

The controller 30 accepts at least one first input signal from at least one first thermistor positioned in contact with the at least one first electrode element, accepts at least one second input signal from at least one second thermistor positioned in contact with the at least one second electrode element, accepts at least one third input signal from at least one third thermistor positioned in contact with the at least one third electrode element, and accepts at least one fourth input signal from at least one fourth thermistor positioned in contact with the at least one fourth electrode element. By processing the first through fourth input signals, the controller can monitor the temperature of each of the electrode elements, and control the current to prevent the electrode elements from overheating. One example of a suitable approach for implementing temperature measurement is the conventional approach used in Optune®. Another example is described in U.S. Pat. No. 11,097,101, which is incorporated herein by reference.

Figure 4:
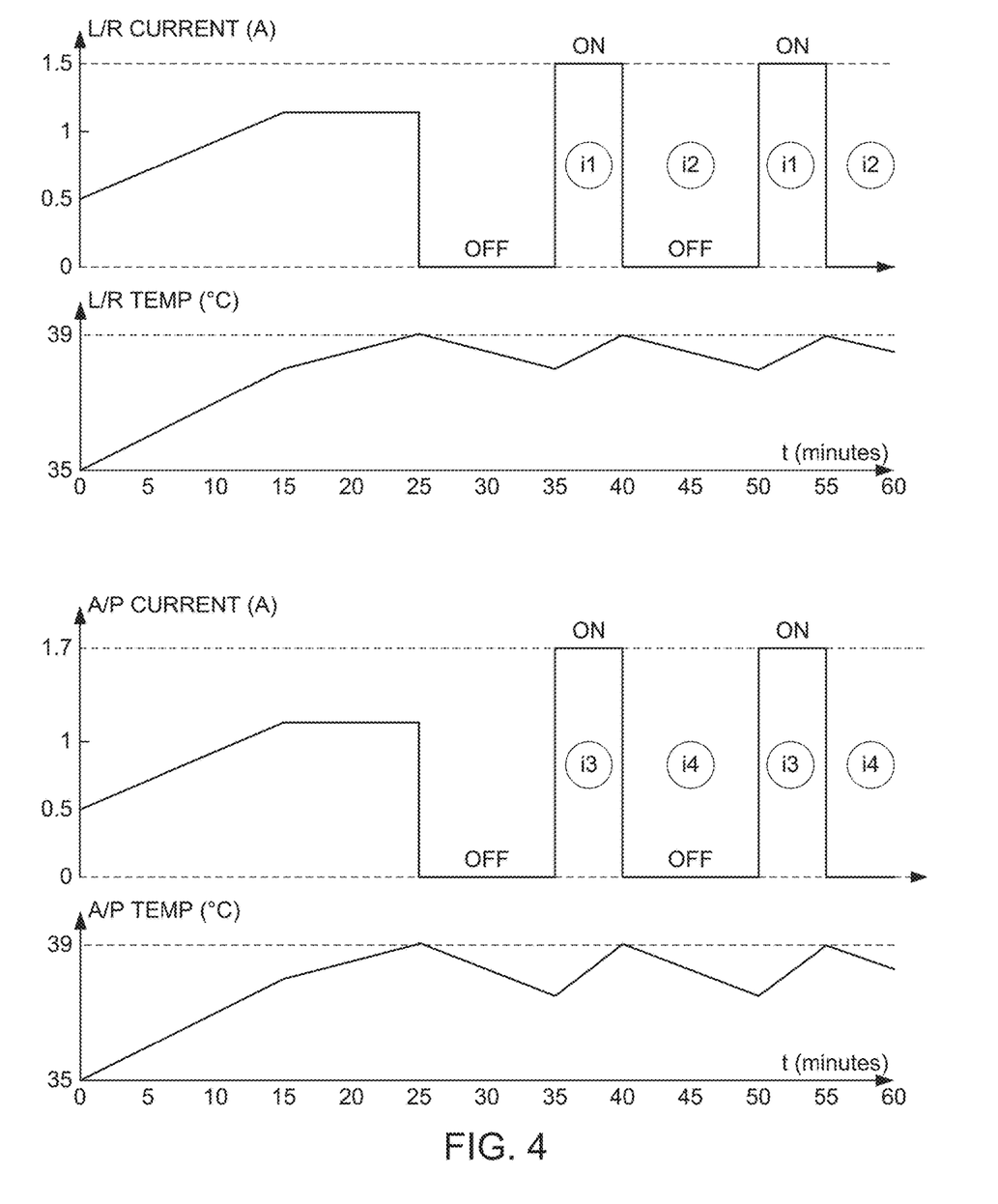
FIG. 4 depicts one example of magnitude profiles for the L/R channel and the A/P channel that can be implemented using the FIG. 3 embodiment in order to generate high-current pulses of alternating current that are interleaved with cooling-down periods.

FIG. 4 depicts one example of magnitude profiles for the L/R channel and the A/P channel that can be implemented using the FIG. 3 embodiment in order to generate high-current pulses of alternating current that are interleaved with cooling-down periods, as well as the corresponding temperature plots for those two channels.

In the FIG. 4 example, both the L/R channel and A/P channel begin their operation as described above in connection with FIG. 1 for the prior art Optune® system between t=0 and t=25 minutes. But instead of stabilizing the current at a level that avoids overheating (e.g., about 1.1 A as described above in connection with FIG. 1), the system does not apply any pulses of alternating current for an interval of time (e.g., between 25 and 35 minutes in FIG. 4), which allows the electrode arrays to cool down (as seen in both temperature plots).

After a sufficient amount of cooling has occurred, the pulses of alternating current start up again during the time interval i1/i3 in response to commands issued by the controller 30. During this time interval, the controller 30 commands the AC signal generator 20 to apply a series of pulses of alternating current between at least one first electrode element 10L and at least one second electrode element 10R, and also apply a series of pulses of alternating current between at least one third electrode element 10A and at least one fourth electrode element 10P. The pulses of alternating current applied to 10L/10R within the time interval i1 have amplitudes at a first level that would cause at least one of the first electrode elements 10L to exceed the temperature threshold *if* the series of pulses was allowed to continue for one hour. (Note how the 1.5 A amplitude for the L/R channel is higher than the 1.1 A amplitude that was used between t=15 and t=25; and also note how the temperature of the electrode elements 10L/10R increases during the time interval i1.) But importantly, the series of pulses is *not* allowed to continue for one hour. Instead, the controller 30 ensures that the series of pulses of alternating current within the time interval i1 is actually short enough to prevent electrode elements 10L and 10R from exceeding the temperature threshold.

The situation is similar for the pulses of alternating current that are applied to 10A/10P within the interval of time i3, except that the amplitude for the A/P channel is 1.7 A in the illustrated example. Note that the current that is applied to the A/P channel can be set independently of the current that is applied to the L/R channel, and each of those currents is set to an amplitude at a level that would cause overheating *if* the series of pulses of alternating current was allowed to continue for one hour.

Because the series of pulses of alternating current within the time interval i1/i3 must be short enough to prevent the electrode elements 10L/10R/10A/10P from exceeding the temperature threshold, the controller 30 issues commands (at t=40 in the FIG. 4 example) to stop the series of high-current pulses of alternating current being applied to the electrode elements 10L/10R and to stop the series of high-current pulses of alternating current being applied to the electrode elements 10A/10P before overheating occurs. The decision to stop the series of high-current pulses could be based on the temperature reaching a threshold (e.g., 37° C., 38° C., 39° C., 40° C., 41° C.), optionally with a maximum time (e.g., after 2, 5, 7, or 10 minutes have elapsed).

i2/i4 is the interval of time that immediately follows i1/i3 after the series of high-current pulses of alternating current have stopped, and during this time interval i2/i4, the controller 30 allows the electrode elements 10L/10R/10A/10P to cool down. (Note how the temperature drops from t=40 to t=50 in the FIG. 4 example.) The time interval i2/i4 is long enough so that a subsequent series of pulses of alternating current can be applied without causing the electrode elements 10L/10R/10A/10P to exceed the temperature threshold. The controller 30 can decide to restart the next series of high-current pulses based on the temperature of the electrode elements 10L/10R/10A/10P reaching a lower threshold (e.g., 34° C., 35° C., 36° C.), optionally with a minimum cooling time (e.g., after 2, 5, 6, 8, or 10 minutes have elapsed). Alternatively, the time interval i2/i4 can be a fixed interval of time (e.g., 5, 6, 8, or 10 minutes).

After the time interval i2/i4 ends, the system alternates back and forth between the situation described above in connection with the time interval i1/i3 (where pulses of alternating current are applied to the electrode elements) and the time interval i2/i4 (where the electrode elements are allowed to cool down). The controller 30 orchestrates this alternation by repeating the commands described above in connection with those time intervals.

The FIGS. 3/4 embodiment has a significant advantage with respect to the prior art Optune® system in that the peak current of the pulses of alternating current in the FIGS. 3/4 embodiment is higher than the peak current for Optune®. And as explained above in connection with FIGS. 2A-2B, TTFields with higher peak currents have higher efficacy than TTFields with lower peak currents, even when the latter are applied over a larger percentage of the available time.

It is important to note that the current magnitude traces in FIG. 4 represent the magnitude of any pulses of alternating current that are generated during a given interval of time. For example, in the example depicted in FIG. 4, the magnitude of each of the pulses of alternating current in the L/R channel is 1.5 A during the intervals of time i1, and the magnitude of each of the pulses of alternating current generated in the A/P channel is 1.7 A during the intervals of time i3. Because the timescale of FIG. 4 is quite long (i.e., 60 minutes) and the duration of each individual pulse could be on the order of 1 second, there could be hundreds of pulses of alternating current within any given interval such as i1/i3.

Figure 5:
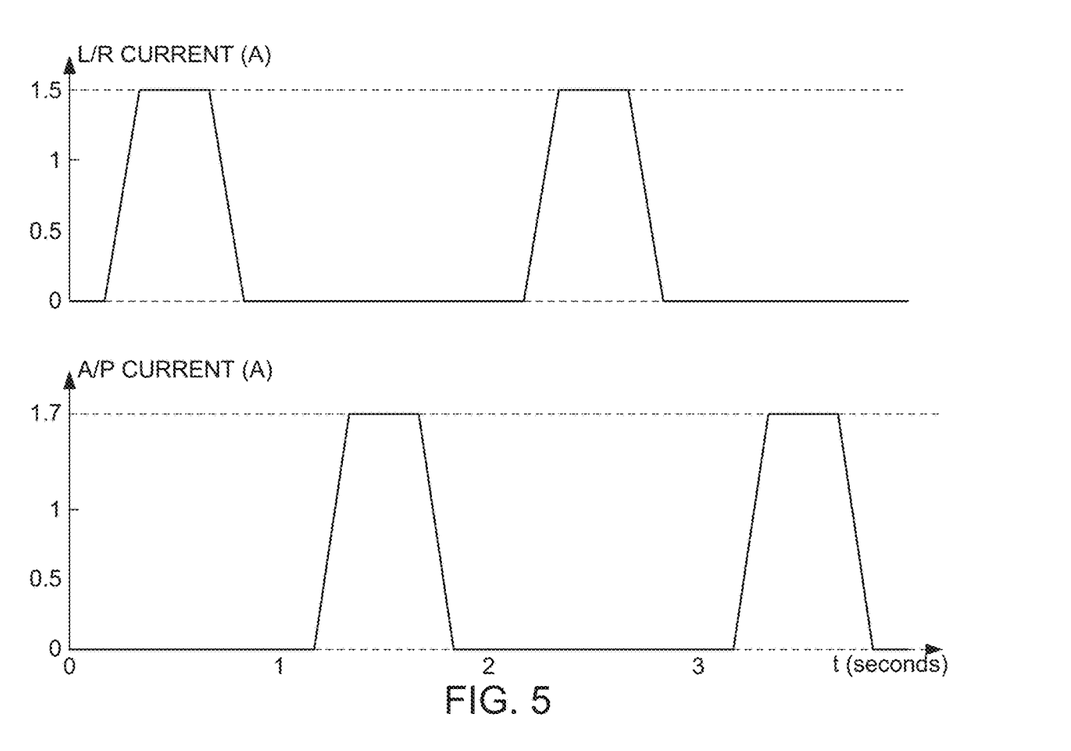
FIG. 5 is a detailed visualization of what the individual pulses of alternating current could look like during the interval of time i1/i3 in the FIG. 4 embodiment.

FIG. 5 is a detailed visualization of what the magnitude of the individual pulses of alternating current could look like during the interval of time i1/i3 in the FIG. 3/4 embodiment. In this FIG. 5 example, the upper trace depicts the magnitude of the first two pulses of alternating current from a series of pulses that are generated every 2 seconds in the L/R channel with a peak current of 1.5 A, and a relatively slow rise time and fall time. Similarly, the lower trace depicts the magnitude of the first two pulses of alternating current from a series of pulses that are generated in the A/P channel every 2 seconds with a peak current of 1.7 A, and a relatively slow rise time and fall time. (The sinusoidal waveform within any given pulse of alternating current is not shown in FIG. 5 because the timescale of the 50 kHz-1 MHz sinusoidal waveform is many orders of magnitude smaller than the timescale of FIG. 5.) Notably, in the example depicted in FIG. 5, the pulses for the L/R channel and the pulses for the A/P channel are out of phase with each other. Note that FIG. 5 depicts just a single illustrative example, and the parameters of these pulses including the pulse repetition times, pulse widths, rise times, fall times, etc. can all be varied.

Returning to FIGS. 3/4, in some embodiments, each of the plurality of cool-down intervals i2/i4 (i.e., 10 minutes in the example depicted in FIG. 4) is at least as long as the immediately preceding pulse-generating interval i1/i3 (i.e., 5 minutes in the example depicted in FIG. 4). In some embodiments, each of the plurality of cool-down intervals is 1-2 times as long as the immediately preceding pulse-generating interval. In some embodiments, each of the plurality of cool-down intervals is 1.5-2.5 times as long as the immediately preceding pulse-generating interval. In some embodiments, each of the plurality of cool-down intervals is 2-3 times as long as the immediately preceding pulse-generating interval.

In some embodiments, the pulses of alternating current in the L/R channel within the intervals of time i1 and the pulses of alternating current in the A/P channel within the intervals of time i3 have amplitudes that are independently controllable. In some embodiments, the pulses of alternating current in the L/R channel within the intervals i1 and the pulses of alternating current in the A/P channel within the intervals i3 have amplitudes that are different. In some embodiments, the pulses of alternating current in the L/R channel within the intervals i1 and the pulses of alternating current in the A/P channel within the intervals i3 have amplitudes that are the same.

In some embodiments, each of the cooling-down intervals i2/i4 is at least 5 minutes. In other embodiments, each of the cooling-down intervals i2/i4 is at least 2, 6, 8, or 10 minutes.

In some embodiments, all the pulses of alternating current in the L/R channel within any given one of the time intervals i1 have the same amplitude. In other embodiments, during each of the time intervals i1, the amplitudes of the pulses of alternating current ramp up (e.g., using a linear ramp-up profile, an exponential ramp-up profile, or a differently-shaped ramp-up profile) from an initial level to a final level and subsequently remain at the final level for the duration of the first time interval.

In some embodiments, including the example depicted in FIG. 4, no pulses of alternating current are applied to the L/R channel or the A/P channel during the cool-down intervals of time i2/i4. Alternatively, low current pulses (i.e., pulses of alternating current with an average amplitude of less than half the average amplitude of the pulses of alternating current that are generated during intervals of time i1/i3) could be applied during the cool-down intervals of time i2/i4.

Note that in the example depicted in FIG. 4, the intervals of time i3 (when the pulses of alternating current are generated in the A/P channel) overlap with the intervals of time i1 (when the pulses of alternating current are generated in the L/R channel)

In some embodiments, there are at least 10 first time intervals i1, at least 10 second time intervals i2, at least 10 third time intervals i3, and at least 10 fourth time intervals i4. In these embodiments, each of the first, second, third, and fourth time intervals i1-i4 is at least one minute long, and each series of pulses includes at least 10 pulses. In some embodiments, there are at least 100 first time intervals i1, at least 100 second time intervals i2, at least 100 third time intervals i3, and at least 100 fourth time intervals i4. Optionally, in these embodiments, each of the first, second, third, and fourth time intervals i1-i4 is at least one minute long, and each series of pulses includes at least 50 pulses. Optionally, in these embodiments, each of the first and third time intervals i1, i3 is independently at least two, three, four, or five minutes long, and each series of pulses within those intervals includes at least 100, 150, 200, or 250 pulses. Optionally, in these embodiments, each of the second and fourth time intervals i2, i4 is independently at least two, three, four, five, six, seven, eight, nine, or ten minutes long, and each series of pulses within those intervals includes at least 100, 150, 200, 250, 300, 350, 400, 450, or 500 low current pulses, or includes no pulses at all.

Figure 6:
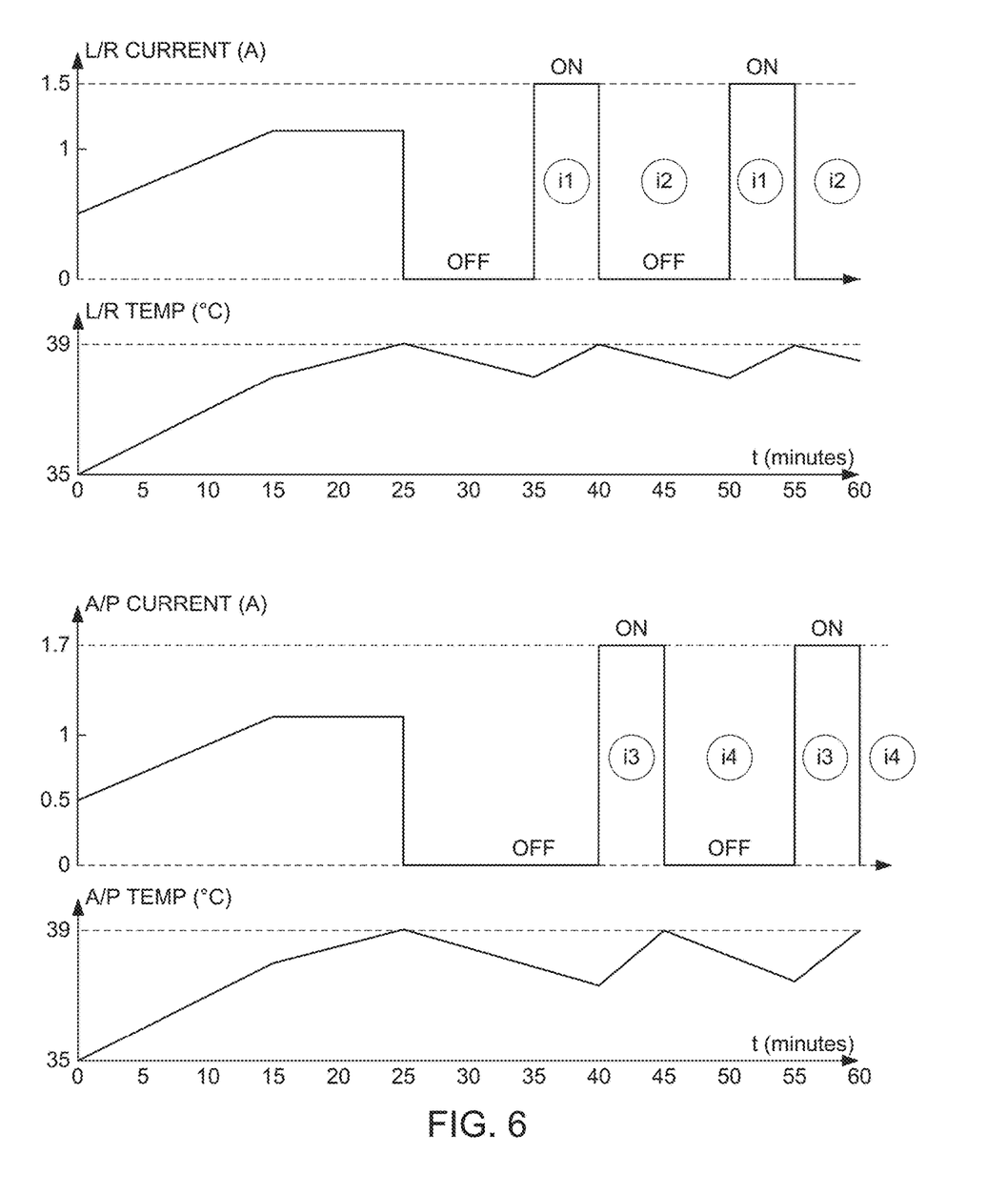
FIG. 6 depicts another example of magnitude profiles for the L/R channel and the A/P channel that can be implemented using the FIG. 3 embodiment in order to generate high-current pulses of alternating current that are interleaved with cooling-down periods.

FIG. 6 depicts another example of magnitude profiles for the L/R channel and the A/P channel that can be implemented using the FIG. 3 embodiment in order to generate high-current pulses of alternating current that are interleaved with cooling-down periods, as well as the corresponding temperature plots for those two channels. This embodiment is similar to the FIG. 4 embodiment described above, except that the high-current pulses of alternating current in the A/P channel are shifted to a different time slot. The first 35 minutes in this FIG. 6 example are the same as in the FIG. 4 example described above.

After a sufficient amount of cooling has occurred, the pulses of alternating current start up again during the time interval i1 in response to commands issued by the controller 30. During this time interval, the AC signal generator 20 applies a series of pulses of alternating current between at least one first electrode element 10L and at least one second electrode element 10R. The pulses of alternating current applied to 10L/10R within the time interval i1 have amplitudes at a first level that would cause at least one of the first electrode elements 10L to exceed the temperature threshold *if* the series of pulses was allowed to continue for one hour. But importantly, the series of pulses is *not* allowed to continue for one hour. Instead, the series of pulses of alternating current within the time interval i1 is actually short enough to prevent electrode elements 10L and 10R from exceeding the temperature threshold.

Because the series of pulses of alternating current within the time interval i1 must be short enough to prevent the electrode elements 10L/10R from exceeding the temperature threshold, the controller 30 issues commands (at t=40 in the FIG. 6 example) to stop the series of high-current pulses of alternating current being applied to the electrode elements 10L/10R before overheating occurs. The decision to stop the series of high-current pulses of alternating current could be based on the temperature reaching a threshold (e.g., 37° C., 38° C., 39° C., 40° C., or 41° C.), optionally with a maximum time (e.g., after 2, 5, 7, or 10 minutes have elapsed).

i2 is the interval of time that immediately follows i1 after the series of high-current pulses of alternating current have stopped, and during this time interval i2, the controller 30 allows the electrode elements 10L/10R to cool down. (Note how the temperature drops from t=40 to t=50 for the L/R channel in the FIG. 6 example.) The time interval i2 is long enough so that a subsequent series of pulses of alternating current can be applied without causing the electrode elements 10L/10R to exceed the temperature threshold. The controller 30 can decide to restart the next series of high-current pulses of alternating current based on the temperature of the electrode elements 10L/10R reaching a lower threshold (e.g., 34° C., 35° C., or 36° C.), optionally with a minimum cooling time (e.g., after 2, 5, 6, 8, or 10 minutes have elapsed).

After the time interval i2 ends, the system alternates back and forth between the situation described above in connection with the time interval i1 (where pulses of alternating current are applied to the electrode elements) and the time interval i2 (where the electrode elements are allowed to cool down). The controller 30 orchestrates this alternation by repeating the commands described above in connection with those time intervals.

The FIGS. 3/6 embodiment has a significant advantage with respect to the prior art Optune® system in that the peak current of the pulses of alternating current in the FIGS. 3/6 embodiment is higher than the peak current for Optune®. And as explained above in connection with FIGS. 2A-2B, TTFields with higher peak currents have higher efficacy than TTFields with lower peak currents, even when the latter are applied over a larger percentage of the available time.

Figure 7:
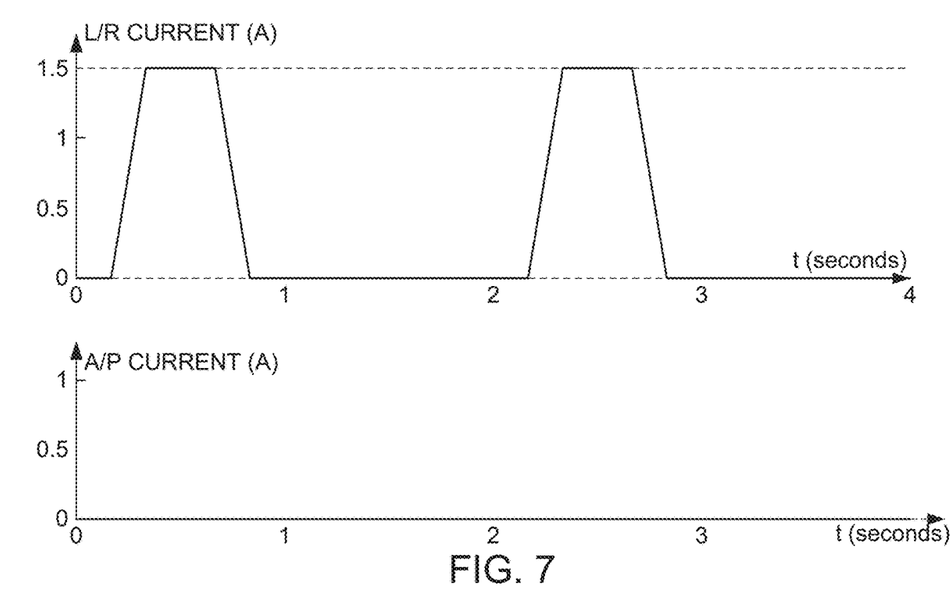
FIG. 7 is a detailed visualization of what the individual pulses of alternating current for the L/R channel could look like during the interval of time i1 in the FIG. 6 embodiment.

Similar to the situation described above in connection with FIG. 4, the current magnitude traces in FIG. 6 represent the magnitude of any pulses of alternating current that are generated during a given interval of time. FIG. 7 is a detailed visualization of what the magnitude of the individual pulses of alternating current for the L/R channel could look like during the interval of time i1 in the FIG. 3/6 embodiment. In this FIG. 7 example, the trace depicts the magnitude of the first two pulses of alternating current from a series of pulses that are generated every 2 seconds in the L/R channel with a peak current of 1.5 A, and a relatively slow rise time and fall time. (The sinusoidal waveform within any given pulse of alternating current is not shown in FIG. 7 because the timescale of the 50 kHz-1 MHz sinusoidal waveform is many orders of magnitude smaller than the timescale of FIG. 7.) Note that FIG. 7 depicts just a single illustrative example, and the parameters of these pulses including the pulse repetition times, pulse widths, rise times, fall times, etc. can all be varied.

The operation of the A/P channel in this FIG. 6 embodiment is similar to the operation of the L/R channel, but offset in time so that the high-current pulses of alternating current in the A/P channel are not generated at the same time as the high-current pulses of alternating current in the L/R channel, and with a 1.7 A current in the A/P channel.

Returning to FIGS. 3/6, in some embodiments, each of the plurality of cool-down intervals i2, i4 (i.e., 10 minutes in the examples depicted in FIG. 6) is at least as long as the immediately preceding pulse-generating interval i1, i3 (i.e., 5 minutes in the examples depicted in FIG. 6). In some embodiments, each of the plurality of cool-down intervals is 1-2 times as long as the immediately preceding pulse-generating interval. In some embodiments, each of the plurality of cool-down intervals is 1.5-2.5 times as long as the immediately preceding pulse-generating interval. In some embodiments, each of the plurality of cool-down intervals is 2-3 times as long as the immediately preceding pulse-generating interval.

In some embodiments, the pulses of alternating current in the L/R channel within the intervals of time i1 and the pulses of alternating current in the A/P channel within the intervals of time i3 have amplitudes that are independently controllable. In some embodiments, the pulses of alternating current in the L/R channel within the intervals i1 and the pulses of alternating current in the A/P channel within the intervals i3 have amplitudes that are different. In some embodiments, the pulses of alternating current in the L/R channel within the intervals i1 and the pulses of alternating current in the A/P channel within the intervals i3 have amplitudes that are the same.

In some embodiments, each of the cooling-down intervals i2, i4 is at least 5 minutes. In other embodiments, each of the cooling-down intervals i2/i4 is at least 2, 6, 8, or 10 minutes.

In some embodiments, all the pulses of alternating current in the L/R channel within any given one of the time intervals i1 have the same amplitude. In other embodiments, during each of the time intervals i1, the amplitudes of the pulses of alternating current ramp up from an initial level to a final level and subsequently remain at the final level for the duration of the first time interval.

In some embodiments, including the example depicted in FIG. 6, no pulses of alternating current are applied to the L/R channel or the A/P channel during the cool-down intervals of time i2, i4. Alternatively, low current pulses (i.e., pulses of alternating current with an average amplitude less than half the average amplitude of the pulses of alternating current that are generated during intervals of time i1, 13) could be applied during the cool-down intervals of time i2, i4.

As noted above, the high-current pulses of alternating current in the A/P channel are shifted to a different time slot in this FIG. 6 embodiment (as compared to the FIG. 4 embodiment). In some embodiments (including the example illustrated in FIG. 6), each third interval of time i3 is mutually exclusive with all the first intervals of time i1, and each first interval of time i1 is mutually exclusive with all the third intervals of time i3.

In some embodiments, there are at least 10 first time intervals i1, at least 10 second time intervals i2, at least 10 third time intervals i3, and at least 10 fourth time intervals i4. In these embodiments, each of the first, second, third, and fourth time intervals i1-i4 is at least one minute long, and each series of pulses includes at least 10 pulses. In some embodiments, there are at least 100 first time intervals i1, at least 100 second time intervals i2, at least 100 third time intervals i3, and at least 100 fourth time intervals i4. Optionally, in these embodiments, each of the first, second, third, and fourth time intervals i1-i4 is at least one minute long, and each series of pulses includes at least 50 pulses. Optionally, in these embodiments, each of the first and third time intervals i1, i3 is independently at least two, three, four, or five minutes long, and each series of pulses within those intervals includes at least 100, 150, 200, or 250 pulses. Optionally, in these embodiments, each of the second and fourth time intervals i2, i4 is independently at least two, three, four, five, six, seven, eight, nine, or ten minutes long, and each series of pulses within those intervals includes at least 100, 150, 200, 250, 300, 350, 400, 450, or 500 pulses, or includes no pulses at all.

Note that in the examples depicted in FIG. 4 and FIG. 6, each of the second time intervals i2 (i.e., the cooling intervals) is depicted as being longer than the immediately preceding first time interval i1 (in which a series of pulses of alternating current is applied between the first electrode elements and at the second electrode elements); and each of the fourth time intervals i4 (i.e., the cooling intervals) is depicted as being longer than the immediately preceding third time interval i3 (in which a series of pulses of alternating current is applied between the third electrode elements and at the fourth electrode elements). But this is not necessarily so in all embodiments. To the contrary, each second time interval i2 could be shorter than the immediately preceding first time interval i1; and each fourth time interval i4 could be shorter than the immediately preceding third time interval i3.

Figure 8:
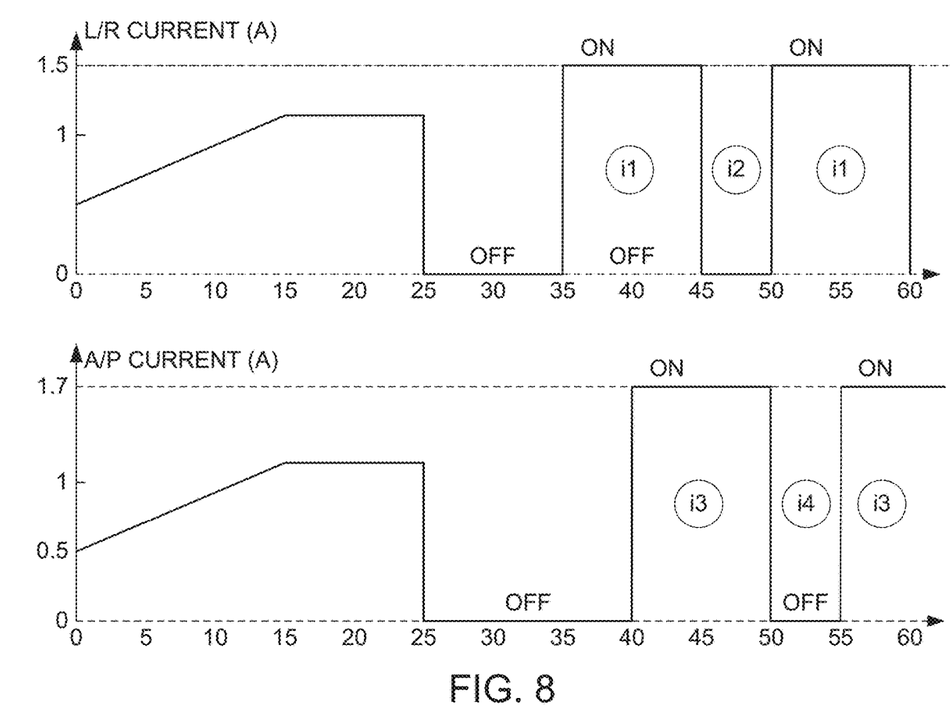
FIG. 8 depicts yet another example of magnitude profiles for the L/R channel and the A/P channel that can be implemented using the FIG. 3 embodiment in order to generate high-current pulses of alternating current that are interleaved with cooling-down periods.

One example of this situation is depicted in FIG. 8, in which each first time interval i1 and each third time interval i3 is 10 minutes long, and each second time interval i2 and each fourth time interval i4 is 5 minutes long. And notably, with this timing relationship, at least one channel (i.e., L/R or A/P) will be operating at its peak current at all times (as seen in FIG. 8). Note that FIG. 8 depicts just a single illustrative example of potential durations for the first through fourth time intervals i1-i4, and those durations can be varied. In one preferred variation of the situation depicted in FIG. 8, each first time interval i1 and each third time interval i3 is 15 minutes long, and each second time interval i2 and each fourth time interval i4 is 10 minutes long. In a second preferred variation of the situation depicted in FIG. 8, each first time interval i1 and each third time interval i3 is 30 minutes long, and each second time interval i2 and each fourth time interval i4 is 15 minutes long. With either of these preferred timing relationships, at least one channel (i.e., L/R or A/P) will be operating at its peak current at all times.

In vivo experimental data revealed that the second preferred variation of the situation depicted in FIG. 8 provided higher currents in both channels simultaneously than the prior art approach used in Optune®. More specifically, at least one of the channels operated at a current above 90 mA 80.2% of the time using the second preferred approach on mice. In contrast, at least one of the channels operated at a current above 90 mA 55.5% of the time using the prior art approach on mice. In addition, the average current using the second preferred approach was 17.45% higher than the prior art approach in one in vivo experiment on mice, and 20.9% higher in another in vivo experiment on mice.

When the first and third time intervals i1, i3 are longer than the second and fourth time intervals i2, i4, the visualization of the magnitude of the individual pulses of alternating current will vary depending on whether one or both channels are active at any given instant. For example, because only the L/R channel is active between t=35 and t=40 in FIG. 8, the magnitude of the individual pulses of alternating current for that interval of time will resemble the situation depicted in FIG. 7. On the other hand, because both channels are active between t=40 and t=45 in FIG. 8, the magnitude of the individual pulses of alternating current for that interval of time will resemble the situation depicted in FIG. 5. Note that FIGS. 5 and 7 depict just a single illustrative example each, and the parameters of these pulses including the pulse repetition times, pulse widths, rise times, fall times, etc. can all be varied.

In the embodiments described above in connection with FIG. 3-8, alternating electric fields are applied to a subject's body (or to an in vitro dish) using two pairs of electrode elements—one pair positioned to the left and right of the target region, and a second pair positioned anterior and posterior to the target region. This configuration is advantageous in many situations, particularly where the alternating electric fields have a directional effect (as is the case with TTFields). But in other situations, alternating electric fields that are only applied in a single direction may suffice. These situations include, for example, using alternating electric fields to increase the permeability of a subject's blood-brain barrier. The hardware for these single-direction embodiments is similar to the hardware depicted in FIG. 3, except that one of the L/R and the A/P channels depicted in FIG. 3 is omitted.

Figure 9:
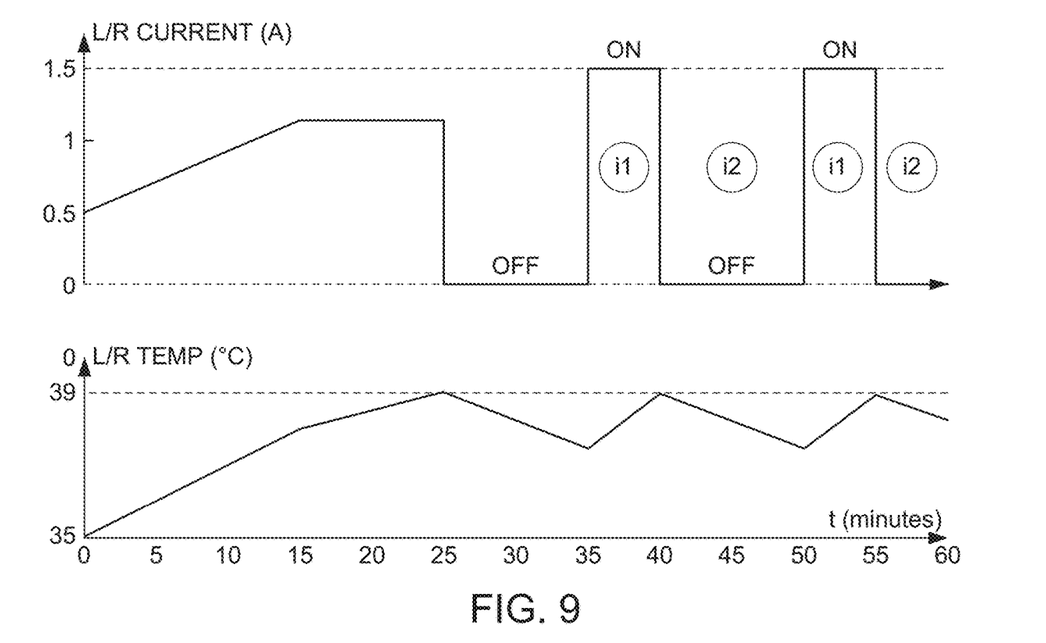
FIG. 9 depicts one example of a magnitude profile that can be implemented using a single-direction embodiment in order to generate high-current pulses of alternating current that are interleaved with cooling-down periods.

FIG. 9 depicts one example of a magnitude profile that can be implemented using this single-direction embodiment in order to generate high-current pulses of alternating current that are interleaved with cooling-down periods, as well as a corresponding temperature plot for the single channel. The operation of the single channel is similar to the operation of the L/R channel described above in connection with FIG. 4. This FIG. 9 embodiment has a significant advantage over the prior art Optune® system in that the peak current of the pulses of alternating current is higher than the peak current for Optune®. And as explained above in connection with FIGS. 2A-2B, TTFields with higher peak currents have higher efficacy than TTFields with lower peak currents, even when the latter are applied over a larger percentage of the available time.

Figure 10:
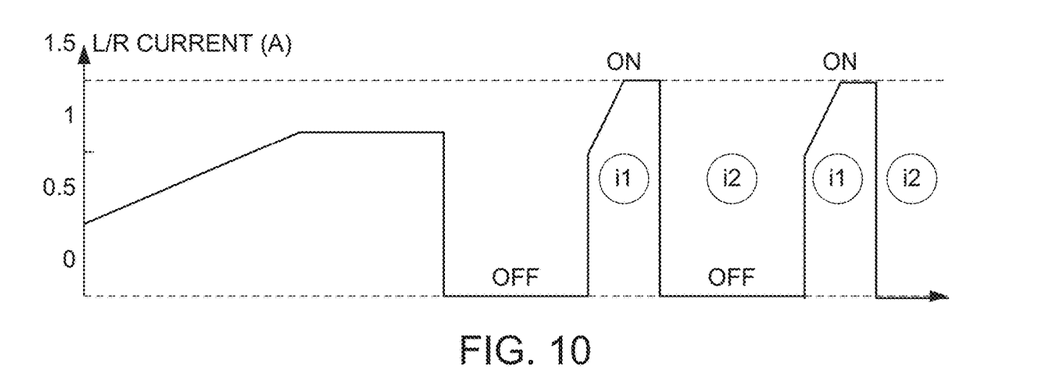
FIG. 10 depicts another example of a magnitude profile that can be implemented using a single-direction embodiment in order to generate high-current pulses of alternating current that are interleaved with cooling-down periods.

FIG. 10 depicts another example of a magnitude profile that can be implemented using this single-direction embodiment in order to generate high-current pulses of alternating current that are interleaved with cooling-down periods, as well as a corresponding temperature plot for the single channel. This example is similar to the FIG. 9 example, except that all the pulses of alternating current in the L/R channel within any given one of the time intervals i1 do not have the same amplitude. Instead, during each of the time intervals i1, the amplitudes of the pulses of alternating current ramp up (e.g., using the depicted linear ramp-up profile, or a different ramp-up profile including but not limited to logarithmic or exponential ramp-up profiles) from an initial level to a final level, and subsequently remain at the final level for the duration of the time interval i1. Optionally, the amplitude of the pulses of alternating current could also ramp down prior to the end of any given time interval i1/i3.

Note that while the ramp up within each time interval i1 is depicted for the first time in connection with FIG. 10, a similar ramp-up feature may be incorporated into any of the time intervals i1, i3 in any of the embodiments discussed above in connection with FIGS. 3-8.

The concepts described above in connection with FIGS. 2-10 may be applied to both in vivo and in vitro settings. In the in vitro experiments described above, the electrical field was capacitively coupled into the culture because the modified Inovitro™ system used conductive electrodes disposed on the outer surface of the dish sidewalls, and the ceramic material of the sidewalls acts as a dielectric. But in alternative embodiments, the electric field could be applied directly to the cells without capacitive coupling (e.g., by modifying the Inovitro™ system configuration so that the conductive electrodes are disposed on the sidewall's inner surface instead of on the sidewall's outer surface).

The concepts described herein can be applied in the in vivo context by applying the alternating electric fields to a target region of a live subject's body. This may be accomplished, for example, by positioning electrodes on or below the subject's skin so that application of an AC voltage between selected subsets of those electrodes will impose the alternating electric fields in the target region of the subject's body. For example, in situations where the relevant cells are located in the subject's lungs, one pair of electrodes could be positioned on the front and back of the subject's thorax, and a second pair of electrodes could be positioned on the right and left sides of the subject's thorax.

In some in vivo embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body.

Although the discussion above focusses on applying alternating electric fields to cancer cells in vitro and/or in vivo, the same concepts can be used when applying alternating electric fields to a subject's body for other purposes, including but not limited to increasing the permeability of the blood brain barrier and increasing the permeability of cell membranes, as described in U.S. Pat. Nos. 10,967,167 and 11,103,698.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for inducing an alternating electric field in a target region in a subject's body, the apparatus comprising:
   a pulse generator configured to generate a series of pulses of alternating current between a first output terminal and a second output terminal, with an amplitude that depends on a state of at least one control input; and
   a controller configured to send signals to the at least one control input that cause the pulse generator to output pulses having a first amplitude between the first output terminal and the second output terminal during each of a plurality of first time intervals,
   wherein the controller is further configured to, during each of a plurality of second time intervals, each of which immediately follows a respective one of the plurality of first time intervals, either (i) send signals to the at least one control input that cause the pulse generator not to output pulses during each of the plurality of second time intervals or (ii) send signals to the at least one control input that cause the pulse generator to output pulses having a second amplitude between the first output terminal and the second output terminal during each of a plurality of second time intervals, wherein the second amplitude is less than half the first amplitude, wherein the controller is further configured to accept at least one first input signal from at least one first temperature sensor and to accept at least one second input signal from at least one second temperature sensor, wherein the plurality of first time intervals includes at least 10 first time intervals, wherein the plurality of second time intervals includes at least 10 second time intervals, wherein each of the plurality of first time intervals is at least one minute long, wherein each of the plurality of second time intervals is at least one minute long, and wherein each series of pulses includes at least 10 pulses.

2. The apparatus of claim 1, wherein each of the plurality of second time intervals is at least 5 minutes long.

3. The apparatus of claim 1, wherein the pulse generator is further configured to generate a series of pulses of alternating current between a third output terminal and a fourth output terminal, with an amplitude that depends on a state of the at least one control input; and wherein the controller is further configured to send signals to the at least one control input that cause the pulse generator to output pulses having a third amplitude between the third output terminal and the fourth output terminal during each of a plurality of third time intervals, wherein the controller is further configured to, during each of a plurality of fourth time intervals, each of which immediately follows a respective one of the plurality of third time intervals, either (i) send signals to the at least one control input that cause the pulse generator not to output pulses during each of the plurality of fourth time intervals or (ii) send signals to the at least one control input that cause the pulse generator to output pulses having a fourth amplitude between the third output terminal and the fourth output terminal during each of a plurality of fourth time intervals, wherein the fourth amplitude is less than half the third amplitude, wherein the controller is further configured to accept at least one third input signal from at least one third temperature sensor and to accept at least one fourth input signal from at least one fourth temperature sensor, wherein the plurality of third time intervals includes at least 10 third time intervals, wherein the plurality of fourth time intervals includes at least 10 fourth time intervals, wherein each of the plurality of third time intervals is at least one minute long, and wherein each of the plurality of fourth time intervals is at least one minute long.

4. The apparatus of claim 3, wherein the controller is further configured to adjust the first amplitude during each of the plurality of first time intervals based on the at least one first input signal and the at least one second input signal, and to adjust the third amplitude during each of the plurality of third time intervals based on the at least one third input signal and the at least one fourth input signal.

5. The apparatus of claim 3, wherein the controller is further configured to end a given first time interval based on the at least one first input signal and the at least one second input signal, and configured to end a given third time interval based on the at least one third input signal and the at least one fourth input signal.

6. The apparatus of claim 3, wherein the controller is further configured to end a given second time interval based on the at least one first input signal and the at least one second input signal, and to end a given fourth time interval based on the at least one third input signal and the at least one fourth input signal.

7. The apparatus of claim 3, further comprising:
at least one first electrode element wired up to the first output terminal;
at least one second electrode element wired up to the second output terminal;
at least one third electrode element wired up to the third output terminal; and
at least one fourth electrode element wired up to the fourth output terminal.

* * * * *